US009642778B1

(12) United States Patent
Yazbeck

(10) Patent No.: US 9,642,778 B1
(45) Date of Patent: May 9, 2017

(54) FEEDING TUBE HOLDER

(71) Applicant: Michael D. Yazbeck, Braintree, MA (US)

(72) Inventor: Michael D. Yazbeck, Braintree, MA (US)

( * ) Notice: Subject to any disclaimer, the term of this patent is extended or adjusted under 35 U.S.C. 154(b) by 0 days.

(21) Appl. No.: 14/936,128

(22) Filed: Nov. 9, 2015

Related U.S. Application Data

(60) Provisional application No. 62/077,273, filed on Nov. 9, 2014.

(51) Int. Cl.
A47D 15/00 (2006.01)
A61J 9/06 (2006.01)
A61J 15/00 (2006.01)
F16L 3/08 (2006.01)
F16L 3/00 (2006.01)
A47F 7/00 (2006.01)
F16M 11/00 (2006.01)
F16M 13/00 (2006.01)
A47G 23/02 (2006.01)
A47B 96/06 (2006.01)
E04G 3/00 (2006.01)
F16B 1/00 (2006.01)
G09F 7/18 (2006.01)
A47F 5/00 (2006.01)
B65D 23/12 (2006.01)
B65D 90/12 (2006.01)
(Continued)

(52) U.S. Cl.
CPC ......... A61J 15/0061 (2013.01); A61J 9/0638 (2015.05); F16L 3/08 (2013.01); A61G 7/0503 (2013.01); A61J 1/16 (2013.01); A61J 9/00 (2013.01); A61J 9/06 (2013.01); A61J 9/0661 (2015.05); A61J 9/0676 (2015.05); A61J 9/0684 (2015.05); A61J 15/0026 (2013.01); A61M 5/008 (2013.01); A61M 5/1415 (2013.01); A61M 5/1417 (2013.01); A61M 2209/08 (2013.01); F16M 11/10 (2013.01); F16M 11/2021 (2013.01); F16M 13/00 (2013.01); F16M 13/022 (2013.01)

(58) Field of Classification Search
CPC .............. A61M 5/1414; A61M 5/1415; A61M 5/1417; A61M 5/008; A61M 2209/08; A61J 15/0053; A61J 15/0065; A61J 15/0638; A61J 15/0661; A61J 9/0638; A61J 9/0661; A61J 9/00; A61J 9/0684; A61J 15/0026; A61J 1/16; A61J 9/06; A61J 9/0676; A61G 7/0503; F16M 13/022; F16M 11/2021; F16M 11/10; F16M 13/00
USPC ............. 248/102–107, 228.4, 230.4, 231.51, 248/231.71, 286.1, 297.31, 311.2, 311.3, 248/312, 121, 125.1, 146, 229.15, 309.1, 248/313; 215/377, 386, 399
See application file for complete search history.

(56) References Cited

U.S. PATENT DOCUMENTS 1,040,659 A * 10/1912 Escherich ................. A61J 9/06
211/74
1,647,039 A 10/1927 Fischer
(Continued)

Primary Examiner — Brian Mattei
Assistant Examiner — Taylor Morris
(74) Attorney, Agent, or Firm — John P. McGonagle

(57) ABSTRACT

A feeding tube holder is provided. The feeding tube holder is attached to a squeeze clamp for attachment to a crib or chair. The holder and squeeze clamp interface is adjustable for a plurality of position changes. Feeding tubes have fastening elements to provide attachment of any type of feeding tube.

1 Claim, 9 Drawing Sheets

(51) Int. Cl.
*F16M 11/20* (2006.01)
*F16M 11/10* (2006.01)
*F16M 13/02* (2006.01)
*A61M 5/00* (2006.01)
*A61J 1/16* (2006.01)
*A61M 5/14* (2006.01)
*A61J 9/00* (2006.01)
*A61G 7/05* (2006.01)

(56) References Cited

U.S. PATENT DOCUMENTS

| | | | |
|---|---|---|---|
| 2,218,311 A | 10/1940 | Elliott | |
| 2,696,963 A * | 12/1954 | Shepherd | A61M 5/1415 24/339 |
| 3,220,434 A | 11/1965 | Garth | |
| 3,298,648 A * | 1/1967 | Sepanski | A61J 9/06 248/103 |
| 4,040,547 A * | 8/1977 | Dickey | F16M 13/04 224/247 |
| D256,661 S | 9/1980 | Graham | |
| 4,367,859 A | 1/1983 | Lamon | |
| 4,463,859 A * | 8/1984 | Greene | A61J 9/00 215/11.1 |
| 4,504,992 A | 3/1985 | Herron et al. | |
| 4,707,906 A * | 11/1987 | Posey | A61G 7/0503 128/DIG. 26 |
| D297,053 S | 8/1988 | Janzen | |
| 5,040,756 A * | 8/1991 | Via Cava | A61J 9/06 248/103 |
| 5,263,941 A | 11/1993 | Cockrill | |
| 5,304,145 A | 4/1994 | Blair | |
| 5,470,037 A * | 11/1995 | Willis | A61G 7/0503 248/125.9 |
| 5,531,702 A * | 7/1996 | Baker | A61M 5/3213 211/85.13 |
| D373,823 S | 9/1996 | Baldwin | |
| 5,853,158 A * | 12/1998 | Riggle | A47G 23/0225 248/103 |
| D425,771 S | 5/2000 | Dearing et al. | |
| 6,129,703 A * | 10/2000 | Beneke | A61J 9/06 604/77 |
| 6,135,983 A | 10/2000 | Andrews et al. | |
| D437,640 S | 2/2001 | Breda et al. | |
| 6,375,132 B1 * | 4/2002 | Tomlinson | D06F 81/003 248/117.6 |
| 6,464,188 B1 * | 10/2002 | Donovan | A61G 7/0503 248/125.1 |
| D468,014 S | 12/2002 | Girod | |
| 6,955,259 B1 * | 10/2005 | Jesse | A61M 5/008 206/366 |
| D512,893 S | 12/2005 | Cowan | |
| 7,458,551 B2 | 12/2008 | Wang et al. | |
| D592,304 S | 5/2009 | Kuehfuss | |
| D622,377 S | 8/2010 | Jackson | |
| 7,850,595 B2 | 12/2010 | White | |
| D651,884 S | 1/2012 | Jansson | |
| D655,593 S | 3/2012 | Wagner, III et al. | |
| D657,054 S | 4/2012 | Bacon | |
| D660,425 S | 5/2012 | Bigelow | |
| 8,220,764 B2 | 7/2012 | Ziaylek | |
| 8,360,953 B2 | 1/2013 | White | |
| D692,132 S | 10/2013 | Damron | |
| D710,994 S | 8/2014 | Yazbeck | |
| 2010/0051491 A1 * | 3/2010 | Lampropoulos | A61M 5/008 206/366 |
| 2010/0057017 A1 * | 3/2010 | Pappas | A61M 5/1417 604/257 |
| 2016/0000993 A1 * | 1/2016 | Endyk | A61M 5/1782 211/85.13 |

* cited by examiner

FEEDING TUBE HOLDER

BACKGROUND OF THE INVENTION

This invention relates to medical feeding devices, and more particularly to a holder for feeding tubes.

There is a need for feeding tubes in a medical environment, both for adults, children and infants. For high-risk neonatal intensive care unit patients the simple task of feeding an infant can be complicated. Ideally, the infant would be held while the infant is being fed. However, this is not always possible, and also neonatal feeding tubes are difficult to handle. Applicant has developed a feeding tube holder, especially useful for neonatal care, for which U.S. Design Pat. No. D710,994 was issued on Aug. 12, 2014 to applicant, hereinafter referred to as the '994 patent or '994 holder. Said design patent is incorporated herein by reference.

In actual use, several limitations with the '994 holder have become apparent. Neonatal infants are tiny. Care of the infants causes support equipment to get bumped and sometimes pushed out of place. Feeding tubes may also come in different forms and sizes, which may require different sized holders. It would also be desirable that the holder be adapted for use with chairs as well as cribs.

SUMMARY OF THE INVENTION

To overcome the limitations of the '994 holder, applicant has changed the clamping structure to provide a larger, flexible clamp which is difficult to push aside and may be used on chairs as well as cribs. Applicant is also providing an adaptable feeding tube holder attachable to the main holder structure. Applicant is also providing a hooking structure adapted to handle nearly any sized feeding tube.

These together with other objects of the invention, along with various features of novelty, which characterize the invention, are pointed out with particularity in the following specification. For a better understanding of the invention, its operating advantages and the specific objects attained by its uses, reference should be had to the accompanying drawings and descriptive matter in which there are illustrated preferred embodiments of the invention.

DETAILED DESCRIPTION OF THE INVENTION

Figure 1:
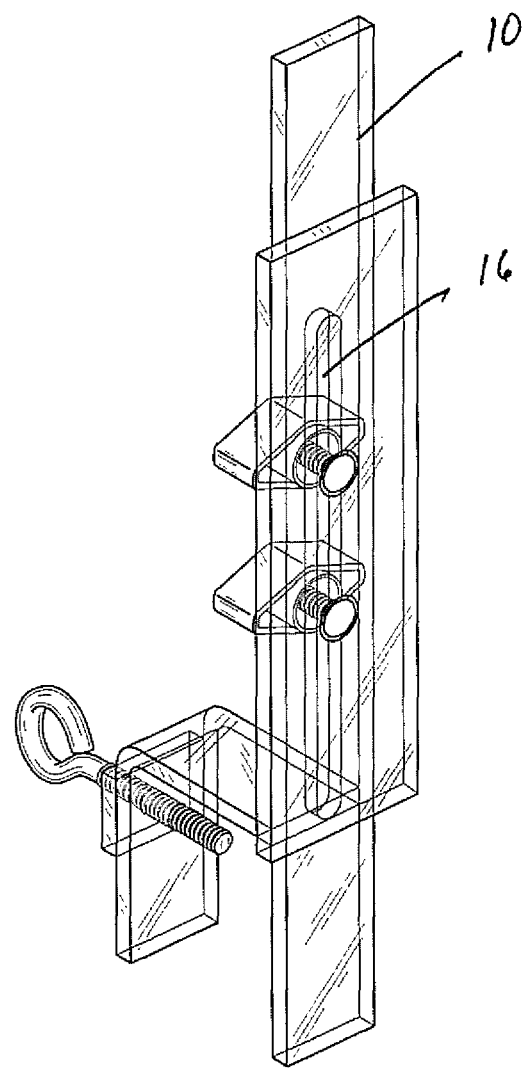
FIG. 1 is a perspective view of the invention of the '994 patent.
Figure 2:
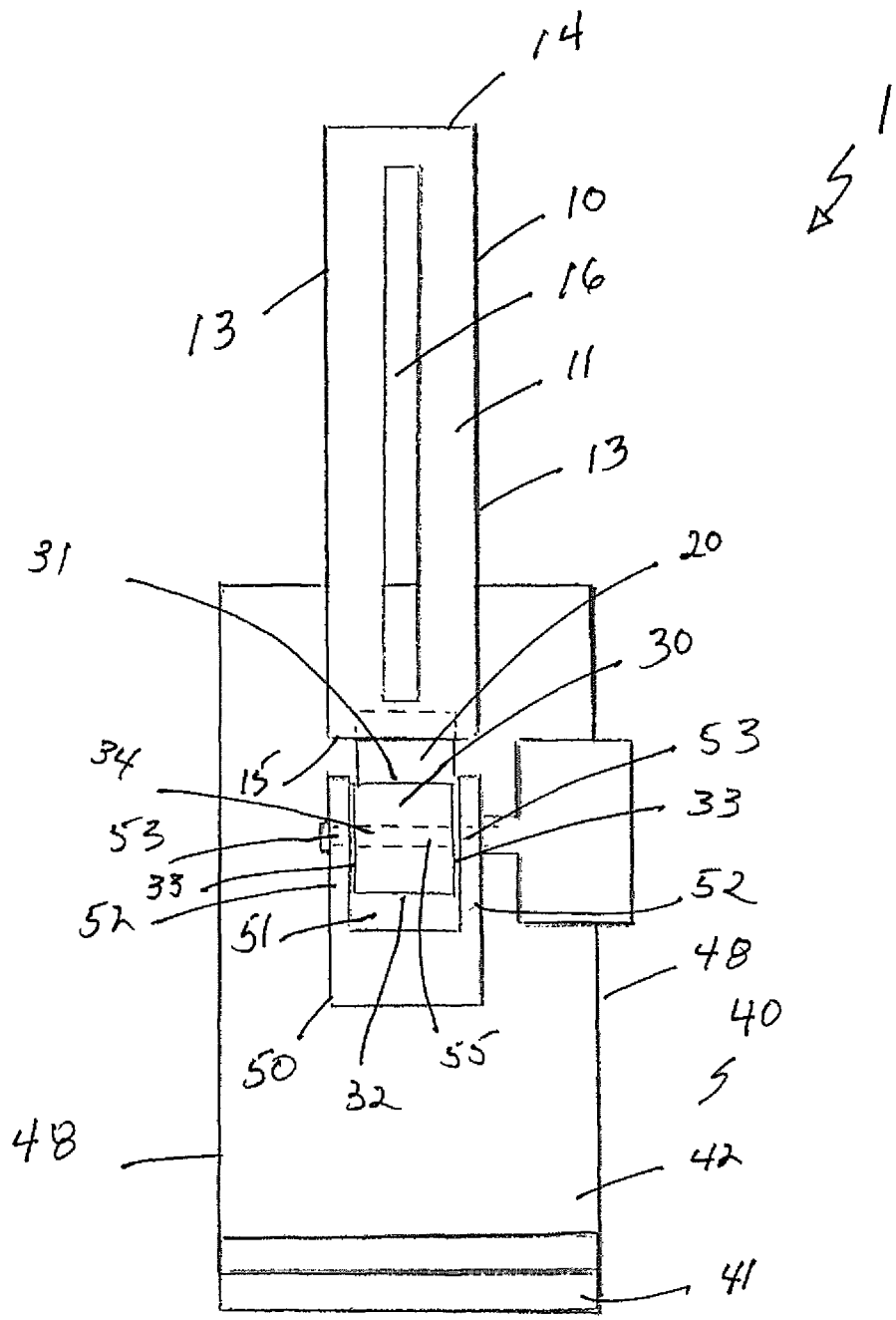
FIG. 2 is a front view of the invention.
Figure 3:
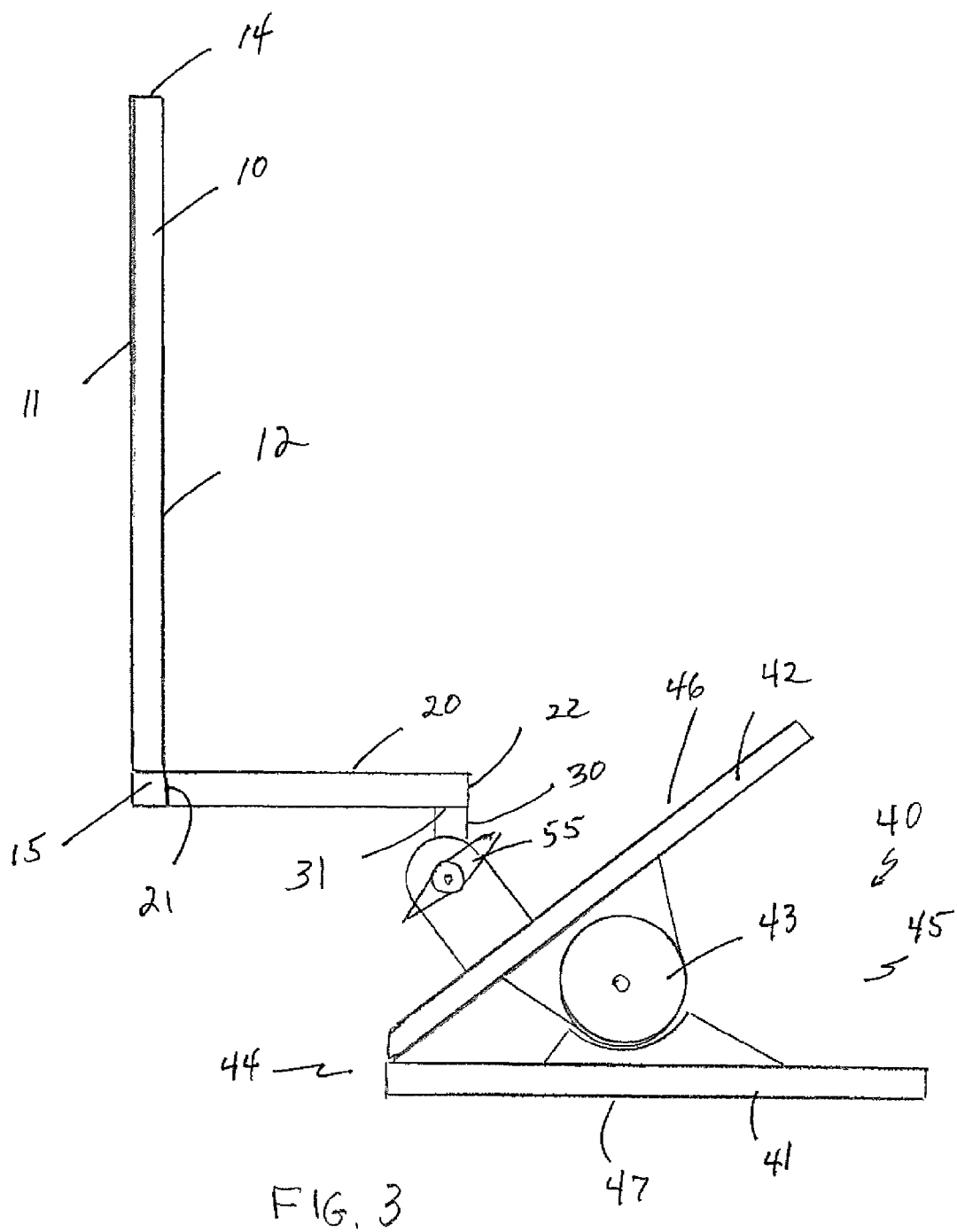
FIG. 3 is a side view of the invention.

Referring to the drawings in detail wherein like elements are indicated by like numerals, there is shown a feeding tube holder according to the principles of the present invention. The feeding tube holder 1 of the present invention is comprised, in part of the generally flat, nominally vertical, elongated holding element 10 having a flat front face 11, opposite flat rear face 12, two opposite side edges 13, a top 14, and a bottom 15. The holding element 10 has an elongated, central channel 16 formed therein, said channel 16 extending nearly to the top 14 and bottom 15. The holding element central channel 16 permits various configurations to be attached to the feeding tube holder 1.

The holding element bottom 15 terminates in perpendicular, rearwardly extending, elongated, element 20. The rearwardly extending element 20 has a first end 21 joined to the holding element bottom 15 and a second, opposite end 22, terminating in a perpendicular, downwardly extending element 30. The downwardly extending element 30 has a first end 31 joined to the rearwardly extending element second end 22 and a second end 32. The downwardly extending element 30 has two opposite sides 33. The downwardly extending element has an aperture 34 centrally formed and extending from one opposite side to the other.

The present invention holder 1 is further comprised of a squeeze clamp 40 comprised of a generally flat bottom arm 41 and a generally flat top arm 42, wherein both arms are pivotally attached to each other by means of a spring-loaded pivot mechanism 43. The squeeze clamp 40 replaces the '944 holder clamping mechanism. The squeeze clamp 40 is oversized and has a front end 44, a rear end 45, a top 46, a bottom 47, and two opposite sides 48, said front end and rear end defining a squeeze clamp longitudinal axis. The pivot mechanism 43 is adapted to keep the arms pressing against each other at the squeeze clamp front end 44, with the arm portions at the squeeze clamp rear end 45 providing means to hand-manipulate the squeeze clamp front end 44 into arm separation. The squeeze clamp top 46 has an attachment element 50 with an upwardly extending, open U-shaped portion 51. The U-shaped portion 51 has two opposite arms 52 defining the U-shape. Each arm 52 has a corresponding aperture 53 defining a nominal axis transverse to the squeeze clamp longitudinal axis. The downwardly extending element 30 is adapted to fit between the U-shaped portion arms 52 and has its aperture 34 in alignment with the U-shaped portion arm apertures 53. An elongated fastener 55 is inserted through the apertures 53 and 34. The fastener 55 is adjustable allowing the downwardly extending element 30 to be horizontally pivoted to various positions, and consequently the rearwardly extending element 20 and vertical holding element 10. The attachment element 50 is also adapted to being pivotally turned and positioned from its nominal position about a vertical axis perpendicular to a top arm 42 plane.

Figure 4:
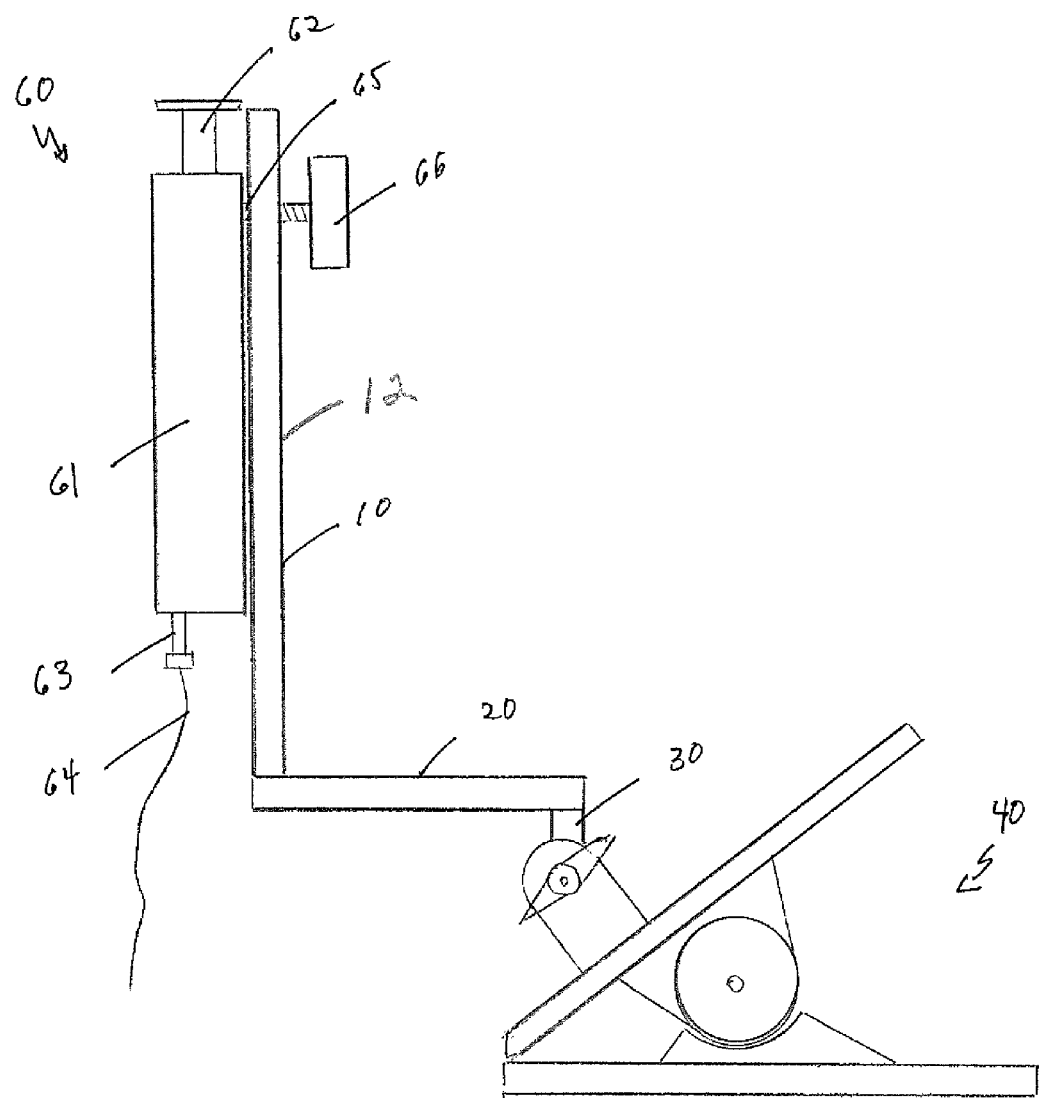
FIG. 4 is a side view of a first embodiment of the invention.

Referring more particularly to FIG. 4, there is shown a modified neonatal feeding syringe 60 attached to the present invention vertical holding element 10. The syringe 60 is comprised of a generally cylindrical casing 61 and a plunger 62, said plunger being removed from the casing when an actual feeding is in operation. The casing 61 has a bottom open protrusion 63 attachable to a feeding tube 64, said casing providing a gravity feed through the open protrusion 63 into and through a feeding tube 64. The casing 61 has a fastening element 65 attached to the syringe casing 61 and protruding axially away therefrom. The casing 61 is positioned against the vertical holding element front face 11. The casing fastening element 65 extends through the vertical element central channel 16 at a desired height and is grasped by a fastener element head 66 against the vertical element rear face 12.

Figure 5:
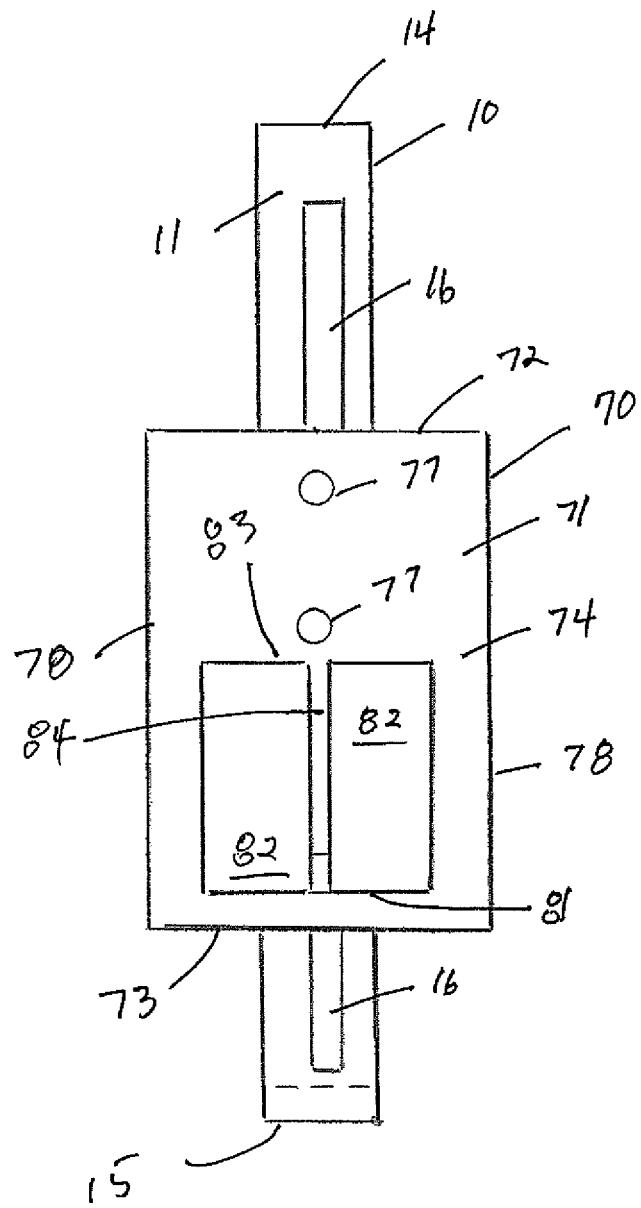
FIG. 5 is a front view of a second embodiment of the invention.
Figure 6:
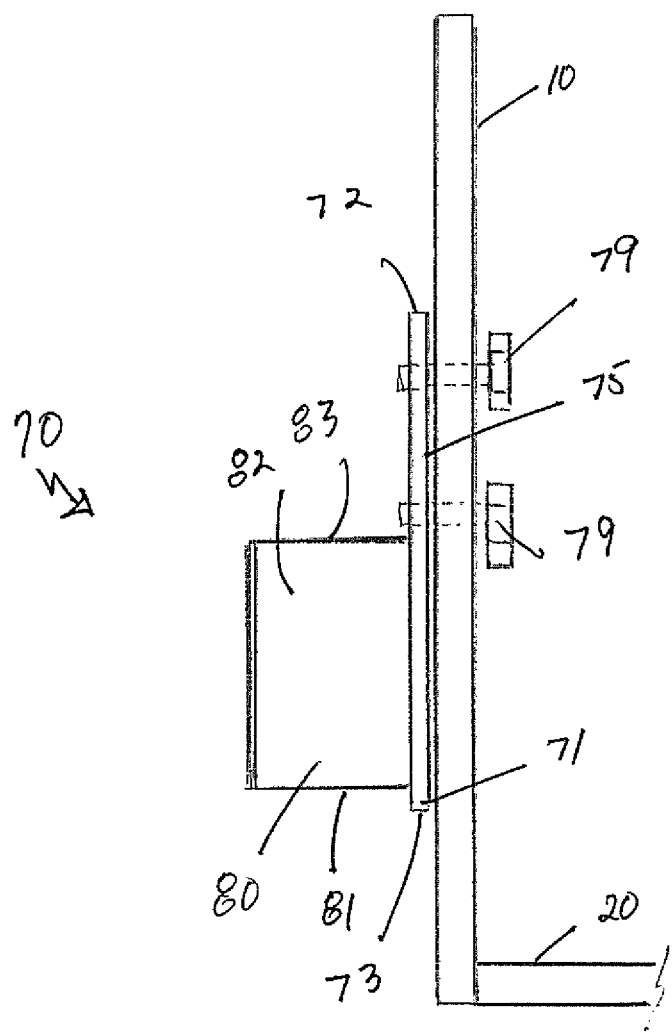
FIG. 6 is a side view of the second embodiment of the invention.
Figure 7:
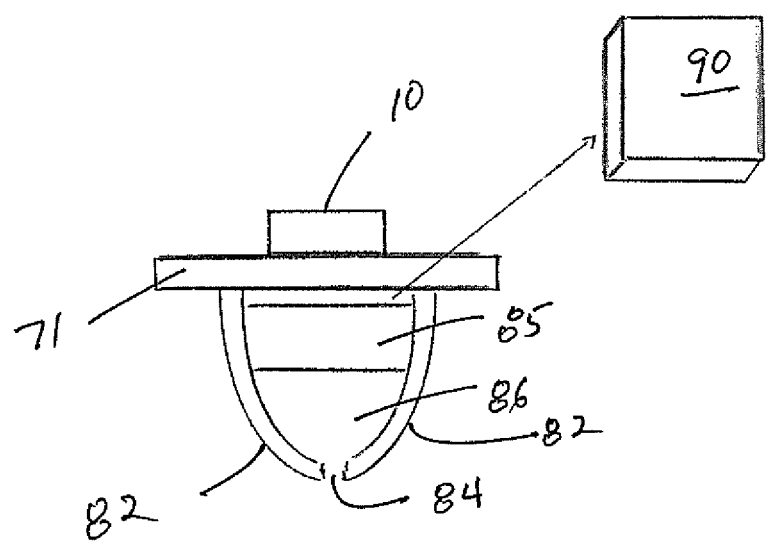
FIG. 7 is a top view of the second embodiment ancillary tube holder.

Referring more particularly to FIGS. 5-7, there is shown a second embodiment of the invention comprising an ancillary tube holder 70 removably fastened to the vertical holding element 10. The ancillary tube holder 70 is comprised of a flat back wall 71, having a top 72, a bottom 73, a front face 74 and a rear face 75. The ancillary tube holder back wall front face 74 has a half-cylindrical element 80 attached thereto starting near to the flat wall bottom 73 and extending upwardly a desired distance toward the flat back wall top 72. The flat back wall 71 has two central apertures 77 formed therein, said apertures 77 arranged vertically above the half-cylindrical element 80. The apertures 77 are adapted to receive removable fasteners 79 extending through the holding element central channel 16, thereby holding the ancillary tube holder 70 to the vertical holding element 10. The half-cylindrical element 80 has a bottom 81, a generally half-cylindrical wall 82 extending upwardly to an open top 83, said half-cylindrical wall 82 terminating on the flat back wall front face 74 near to opposite flat back wall side edges 78. The half-cylindrical wall 82 has a vertical, open, front channel 84 extending centrally from the half-cylindrical element bottom 81 to open top 83. The half-cylindrical bottom 81 has a closed portion 85 extending across the side wall 82 to the flat back wall front face 74. A bottom open portion 86 is formed extending forwardly from the closed portion 85 to the vertical open channel 84. The ancillary tube holder 70 is adapted to hold a feeding syringe casing 61 within the half-cylindrical element 80. The half-cylindrical wall vertical open channel 84 and bottom open portion 86 are adapted to receive the casing bottom open protrusion 63 and feeding tube 64. Spacers 90 may also be used between the casing 61 and the flat back wall front face 74 to hold the casing 61 firmly in place.

Figure 8:
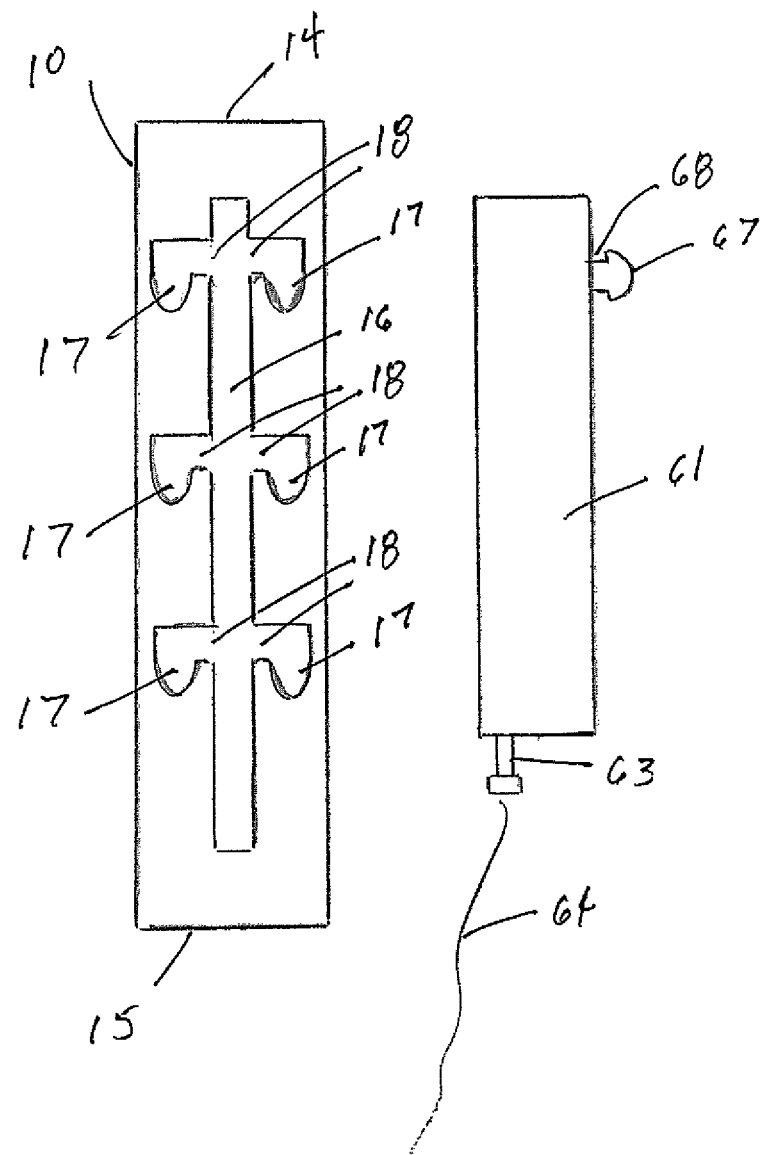
FIG. 8 is a front view of a third embodiment of the invention.
Figure 10:
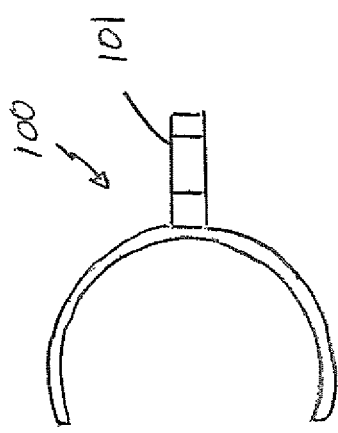
FIG. 10 is a bottom view of the clip.
Figure 9:
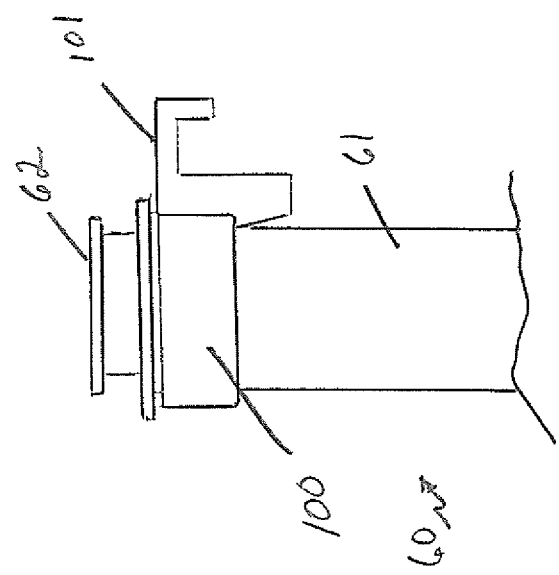
FIG. 9 is a side view of the clip holding a syringe

Referring more particularly to FIG. 8, there is shown a third embodiment of the invention wherein the vertical, elongated holding element 10 is modified to provide two vertical rows of apertures 17, each row adjacent the central channel 16. Each aperture 17 has an open connection 18 to the central channel 16. The neonatal feeding syringe casing fastening element 65 may be comprised of a button 67 with an indented channel 68 about the button circumference. The button 67 is positioned within the central channel 16 and then slid across the open connection 18 into an aperture 17 wherein the indented channel 65 engages the aperture edge holding the casing in a desired position against the holding element 10.

Alternatively, a syringe-holding clip 100 may be provided. The clip 100 is adapted to slidably fit about the syringe casing 61. The clip 100 has a protruding hook 101 adapted to fit into one of the apertures 17 and suspend the syringe 60 from the holding element 10.

It is understood that the above-described embodiments are merely illustrative of the application. Other embodiments may be readily devised by those skilled in the art which will embody the principles of the invention and fall within the spirit and scope thereof.

I claim:

1. A feeding tube holder for a neonatal feeding syringe having a generally cylindrical casing and a plunger, said casing having a bottom open protrusion attachable to a feeding tube, said casing providing a gravity feed through the open protrusion into and through a feeding tube, comprising:
   a generally flat, nominally vertical, elongated holding element having a flat front face, an opposite flat rear face, two opposite side edges, a top and a bottom, said holding element having an elongated, central channel extending near to the top and bottom;
   wherein the holding element bottom terminates in a perpendicular, rearwardly extending, elongated, element, said rearwardly extending element having a first end joined to the holding element bottom and a second, opposite end, terminating in a perpendicular, downwardly extending element, said downwardly extending element having a first end joined to the rearwardly extending element second end and a second end, said downwardly extending element having two opposite sides, said downwardly extending element having an aperture centrally formed and extending from one opposite side to the other;
   a squeeze clamp comprised of a generally flat bottom arm and a generally flat top arm, wherein both arms are pivotally attached to each other by means of a spring-loaded pivot mechanism, said squeeze clamp having a front end, a rear end, a top, a bottom, and two opposite sides, said front end and rear end defining a squeeze clamp longitudinal axis, said pivot mechanism adapted to keep the arms pressing against each other at the squeeze clamp front end, with the arm portions at the squeeze clamp rear end providing means to hand-manipulate the squeeze clamp front end into arm separation;
   wherein the squeeze clamp top has an attachment element with an upwardly extending, open U-shaped portion having two opposite arms defining a U-shape, each said arm having a corresponding aperture defining a nominal axis transverse to the squeeze clamp longitudinal axis, wherein the downwardly extending element is adapted to fit between the U-shaped portion arms and has its aperture in alignment with the U-shaped portion arm apertures;
   an elongated fastener inserted through the arm apertures and the downwardly extending element aperture, said elongated fastener adjustable allowing the downwardly extending element to be horizontally pivoted to a plurality of positions, and consequently the rearwardly extending element and vertical holding element;
   wherein said attachment element is adapted to being pivotally turned and positioned from a nominal position about a vertical axis perpendicular to a top arm plane;
   wherein said syringe casing has a fastening element attached thereto and protruding axially away therefrom along its own axis, said casing positioned against the vertical holding element front face, said casing fastening element extending through the vertical element central channel at a desired height, wherein said casing fastening element is grasped by a fastener element head against the vertical element rear face.

\* \* \* \* \*